(12) United States Patent
Mittermeyer et al.

(10) Patent No.: US 8,251,955 B2
(45) Date of Patent: Aug. 28, 2012

(54) CATHETER STYLET WITH CATHETER ACCOMMODATING LUMEN

(75) Inventors: Stephan Mittermeyer, Landshut (DE); Christoph Pedain, Menzingen (CH)

(73) Assignee: Brainlab AG, Feldkirchen (DE)

( * ) Notice: Subject to any disclaimer, the term of this patent is extended or adjusted under 35 U.S.C. 154(b) by 90 days.

(21) Appl. No.: 12/326,981

(22) Filed: Dec. 3, 2008

(65) Prior Publication Data

US 2009/0143736 A1 Jun. 4, 2009

Related U.S. Application Data

(60) Provisional application No. 60/992,468, filed on Dec. 5, 2007.

(30) Foreign Application Priority Data

Dec. 3, 2007 (EP) ..................................... 07122132

(51) Int. Cl.
*A61M 5/178* (2006.01)
*A61F 11/00* (2006.01)

(52) U.S. Cl. ......... 604/164.11; 604/164.09; 604/164.01; 606/108

(58) Field of Classification Search ............. 604/164.12, 604/164.01, 164.05, 158–172; 606/108
See application file for complete search history.

(56) References Cited

U.S. PATENT DOCUMENTS

| | | | |
|---|---|---|---|
| 3,330,278 A * | 7/1967 | Santomieri ................... 604/161 |
| 3,359,978 A * | 12/1967 | Smith, Jr. ...................... 604/161 |
| 3,537,451 A * | 11/1970 | Beck et al. ............... 604/165.03 |
| 3,584,625 A * | 6/1971 | Swick ........................... 604/161 |
| 3,651,807 A * | 3/1972 | Huggins ....................... 604/161 |
| 3,656,479 A * | 4/1972 | Huggins ....................... 604/161 |
| 3,677,244 A * | 7/1972 | Hassinger ..................... 604/161 |
| 4,046,144 A | 9/1977 | McFarlane |
| 4,079,738 A * | 3/1978 | Dunn et al. ............. 604/164.05 |
| 5,098,411 A | 3/1992 | Watson et al. |
| 5,429,118 A * | 7/1995 | Cole et al. ..................... 600/121 |
| 5,665,052 A | 9/1997 | Bullard |
| 5,693,030 A * | 12/1997 | Lee et al. ...................... 604/117 |
| 2004/0138562 A1 | 7/2004 | Makower et al. |
| 2004/0215143 A1 | 10/2004 | Brady et al. |

FOREIGN PATENT DOCUMENTS

WO 2004/062718 7/2004

OTHER PUBLICATIONS

International Search Report for corresponding European Application No. 07 12 2132 dated Jul. 15, 2008.

* cited by examiner

*Primary Examiner* — Manuel A. Mendez
*Assistant Examiner* — Leah Stohr
(74) *Attorney, Agent, or Firm* — Renner, Otto, Boisselle & Sklar, LLP

(57) ABSTRACT

The invention relates to a catheter stylet for stiffening a catheter during the placing process, wherein the stylet comprises an accommodating lumen for at least one fluid-guiding line of the catheter. It also relates to a catheter stylet catheter system, comprising such a stylet and comprising a catheter which comprises a fluid-guiding line, and to a method for stiffening a catheter during the placing process, wherein a stylet which comprises an accommodating lumen is arranged around at least one fluid-guiding line of the catheter.

20 Claims, 4 Drawing Sheets

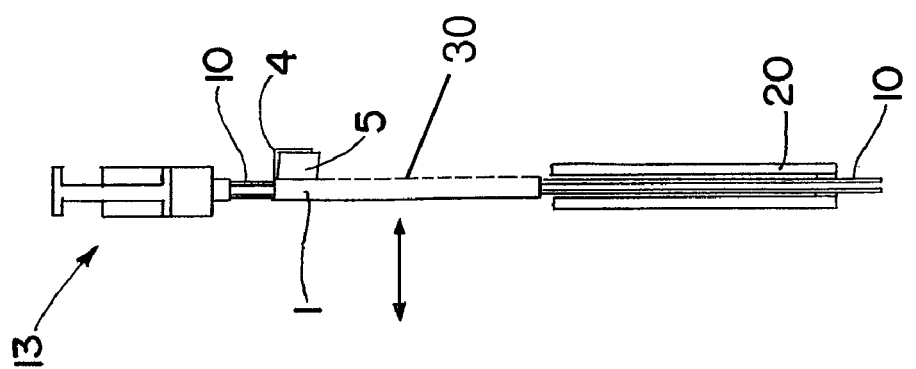

CATHETER STYLET WITH CATHETER ACCOMMODATING LUMEN

RELATED APPLICATION DATA

This application claims the priority of U.S. Provisional Application No. 60/992,468, filed on Dec. 5, 2007, which is hereby incorporated in its entirety by reference.

FIELD OF THE INVENTION

The invention relates to the technical field of stiffening the stylet of a catheter during the catheter placing process. In particular, it relates to a catheter stylet, and specifically to a stylet for a catheter which is used within the framework of a CED (convection-enhanced delivery) treatment.

BACKGROUND OF THE INVENTION

A CED treatment, i.e. a convection-enhanced delivery treatment, is a neurosurgical application in which a catheter is introduced into solid brain tissue, in order to dispense an active agent and/or drug in said brain tissue over a longer period of time and in very small amounts. In order to enable such a catheter to be placed along a planned trajectory, a stylet is needed which provides the necessary stability for the catheter during placement, in order to be able to penetrate all the surfaces in the tissue. After the placing process, the stylet is removed and the catheter which remains in the tissue is then soft and/or flexible in accordance with its material, such that traumas are prevented.

A hollow stylet for an infusion catheter system is known from US 2004/0215143 A1, wherein the hollow stylet is filled with a drug while the catheter is placed together with the stylet. When the stylet, which has been accommodated in the fluid-guiding catheter line for placing, is removed, the drug inserted in the hollow stylet is supposed to remain in the catheter line, thus minimizing the formation of air bubbles in the catheter line after the stylet is removed.

A backflow catheter comprising a hollow stylet is known from U.S. Pat. No. 5,098,411, and U.S. Pat. No. 4,046,144 describes a catheter placement assembly comprising a rigid needle and a special connection system.

Catheter placing systems comprising stylets which are not hollow have, to an even greater extent, the problem that air remains in the fluid-guiding catheter line when the stylet is removed, wherein such air bubbles are extremely problematic, especially in the field of CED applications. The air penetrates into the administering region first, where it takes up space. This leads to a longer backflow region and an unpredictable distribution of the drug in the tissue, which in turn calls the treatment outcome into question. Air mainly penetrates into the catheter for two reasons. One reason is removing the stylet arranged in the fluid-guiding catheter line, as already described above. Another reason is the connecting process to the drug supply unit. Air is likewise introduced into the infusion line during this connecting process, because the air is pushed into the line in the accommodating part of the Luer adaptor by the penetrating part of the Luer adaptor.

SUMMARY OF THE INVENTION

It is the object of the present invention to overcome at least some of the disadvantages described above. The intention is in particular to provide an embodiment of a catheter stylet which simplifies manipulating and placing the catheter and improves treatment outcomes, in particular in CED applications.

This object is solved by: a catheter stylet for stiffening a catheter during the placing process, wherein the stylet comprises an accommodating lumen for at least one fluid-guiding line of the catheter; a catheter stylet catheter system comprising such a stylet and a catheter which comprises a fluid-guiding line; and a method for stiffening a catheter during the placing process, wherein a stylet which comprises an accommodating lumen is arranged around at least one fluid-guiding line of the catheter. The sub-claims define preferred embodiments of the invention.

The catheter stylet in accordance with the present invention is configured such that it comprises an accommodating lumen for at least one fluid-guiding line of the catheter. In other words, the stylet in accordance with the invention is a stylet which can accommodate the fluid-guiding line of the catheter in the accommodating lumen. This solution is thus the exact opposite of the prior art, in which the stylet is always accommodated in the fluid-guiding line of the catheter, while the catheter is being placed.

The solution in accordance with the invention has manifold advantages. One of the most important relates of course to the fact that a catheter which is supported from without by a stylet in accordance with the invention can be pre-filled, i.e. "primed", with a drug. The exterior stylet can then be removed, without the pre-filled status of the catheter changing in any way, and in particular without the fluid-guiding line having to be opened again in order to remove the stylet. In this way, air is positively prevented from penetrating into the catheter. The catheter can also already be connected beforehand to its supply device (syringe or pump for the drug), and this connection does not have to be opened again in order to remove the stylet. It is thus likewise possible to prevent air from penetrating due to connecting processes.

The invention also uses the fact that a hollow stylet, i.e. a stylet with an accommodating lumen, can exhibit substantially the same stiffness as solid-material stylets, in particular when—as with the present invention—it is placed around the outside of a line and for this reason alone exhibits a slightly larger diameter. For this reason, the stiffening function of the stylet can be fulfilled at least as well if not better than in the prior art, and the placing process can follow predetermined trajectories without further ado.

In a preferred embodiment of the invention, an access for the accommodating lumen is provided on the stylet, or an access for the accommodating lumen can be provided on the stylet, in order to introduce at least the fluid-guiding line of the catheter into the lumen or to remove it from the lumen. The stylet can comprise a substantially cylindrical or tubular, elongated body, and in this case, the accommodating lumen is the interior space of the body. It is possible to configure or provide the access such that the stylet can be attached around the line or removed from the line laterally and/or substantially transverse to the profile of the line.

Thus, the fluid-guiding line of the catheter enters the stylet via said access. This access can be a longitudinal slit in the stylet body, a weak point running longitudinally and/or axially on the stylet body, in particular a perforation of the stylet material, or the access can comprise two overlapping longitudinal edges on the body of the stylet. It is possible to form the stylet body as a rolled film, and a lever device can be arranged on the body of the stylet, using which the stylet can be gripped or altered in its diameter, in particular for opening or closing the access which is formed by two overlapping or mutually abutting stylet body longitudinal edges. A rolled film stylet has on the one hand sufficient stiffness in order to be able to place the catheter correctly, and on the other hand is flexible enough to be rolled up, such that it can be removed from the catheter.

The stylet can comprise a plurality of material layers or film layers, in particular a different number of layers along the length of the stylet, which can also form a conically shaped stylet, as can at least one material strip, in particular film strip, which is rolled together at an angle. Such a stylet, which is shaped slightly conically, is simple to remove; however, it is also possible to provide different levels of stiffness along the length of the stylet, if this is necessary.

In another embodiment variant of the invention, the stylet is formed telescopically, and/or one stylet body having a slightly smaller diameter rests in another stylet body, wherein both stylet bodies can comprise an open access longitudinal gap, and these gaps have to be placed one on top of the other, if the stylet is to be removed from the catheter laterally. Such concentric or telescopic stylets can enable the length to be adjusted, or also the stiffness to be increased.

A catheter stylet in accordance with the present invention can comprise one or more of the following materials or can be made from a material which exhibits one or more of the following material properties:

a metal or metal film;
a plastic or plastic film, in particular a polymer, especially PE, PP or PEEK;
a composite material or composite material film;
a memory metal or memory alloy;
a material which is CT-compatible and/or visible in CT images;
a material which is MR-compatible and/or visible in MR images;
a biocompatible material.

The invention also relates to a catheter stylet catheter system comprising: a stylet such as has been discussed above in various embodiments; and a catheter which comprises a fluid-guiding line.

In accordance with one embodiment of this system in accordance with the invention, the catheter has an interior fluid-guiding line and an exterior covering catheter part, and the stylet is provided for insertion between the line and the covering catheter part, such that it surrounds the line and is or can be surrounded by the covering catheter part.

In a system in accordance with the present invention, a removing or opening device can be arranged on the fluid-guiding line, in order to facilitate removing and/or opening the stylet. It is especially possible to configure this device as a cone element or funnel element.

The invention also comprises a method for stiffening a catheter during the placing process, wherein a stylet which comprises an accommodating lumen is arranged around at least one fluid-guiding line of the catheter, wherein a stylet such as has been described above in various embodiment variants can be used.

BRIEF DESCRIPTION OF THE DRAWINGS

The invention is illustrated in more detail below on the basis of embodiments and with the aid of the enclosed drawings. It can comprise any of the features described here, individually and in any expedient combination.

FIG. 9 shows another representation of the stylet-catheter system, when placing and/or removing the stylet.

DETAILED DESCRIPTION

Figure 1:
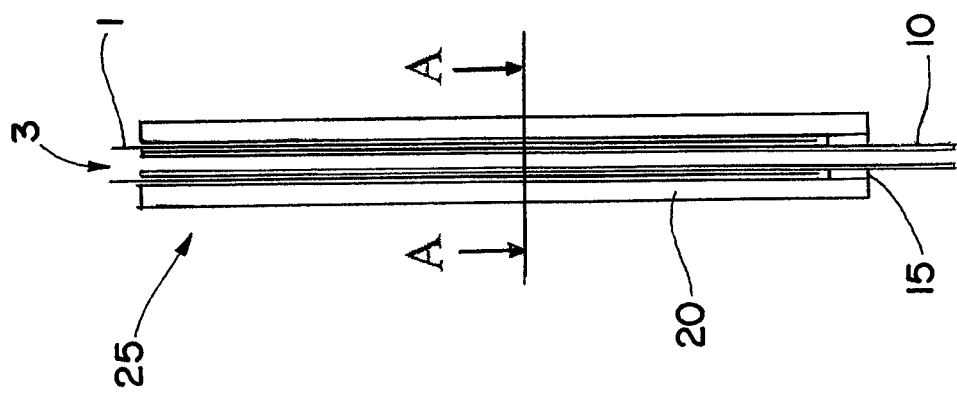
FIG. 1 shows a longitudinal section through a catheter comprising an inserted catheter stylet in accordance with the invention.

FIG. 1 shows a catheter stylet 1 in accordance with the invention in a catheter system. The catheter system comprises the interior fluid-guiding line 10 and the exterior catheter cover 20, wherein the lower end of the line 10 shown in FIG. 1 is the output end for the drug. This output end 10 is supported in the cover 20 by a socket-like element 15.

Figure 2:
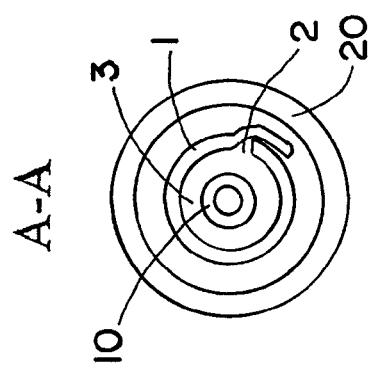
FIG. 2 shows an enlarged section A-A from FIG. 1.

As shown in FIG. 1, and as can also be gathered from the enlarged and exploded sectional view in FIG. 2, the stylet 1 in accordance with the invention surrounds the fluid-guiding line 10 of the catheter, and the stylet is itself surrounded in turn by the catheter cover (covering catheter part) 20.

In the state shown in FIG. 1, the stylet 1—with the line 10 lying in its lumen 3—ensures the stiffness of the catheter during the placing process.

Figure 3:
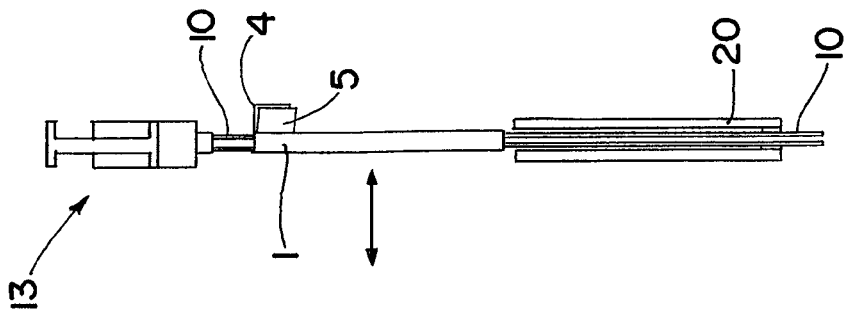
FIG. 3 shows a representation of the stylet-catheter system, when placing and/or removing the stylet.
Figure 4:
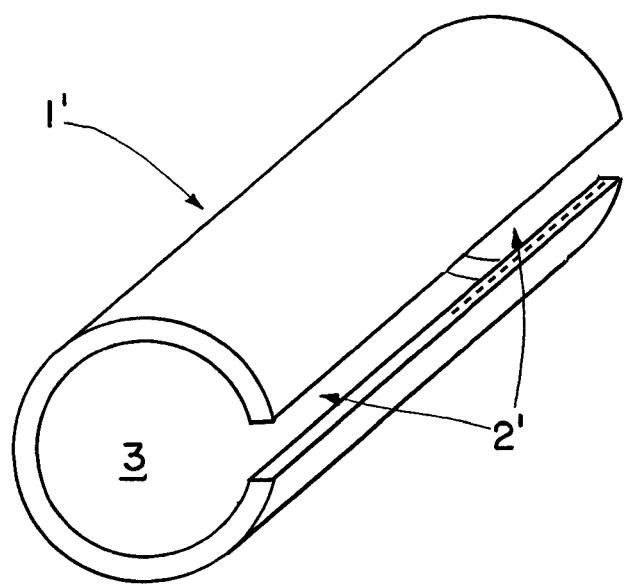
FIGS. 4 and 5 show different embodiments of a rolled film stylet.
Figure 5:
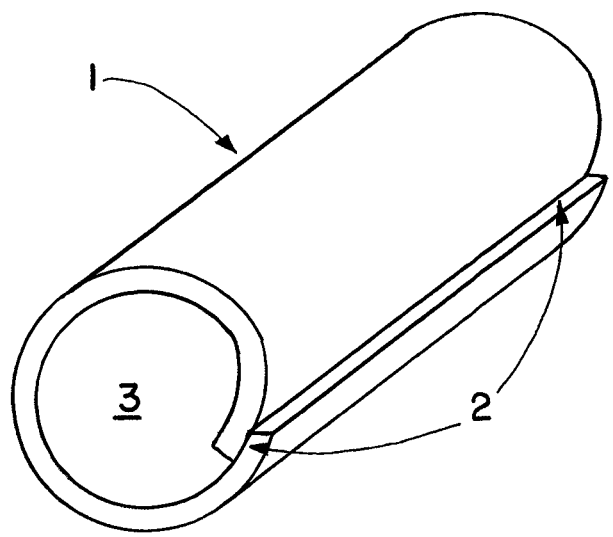
Figure 6:
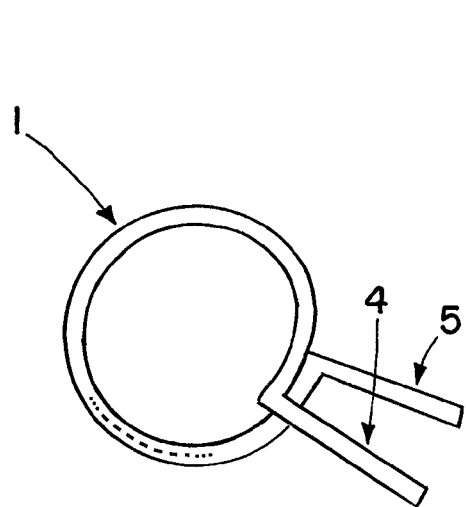
FIGS. 6 and 7 show a lever assembly for manipulating a rolled film stylet.
Figure 7:
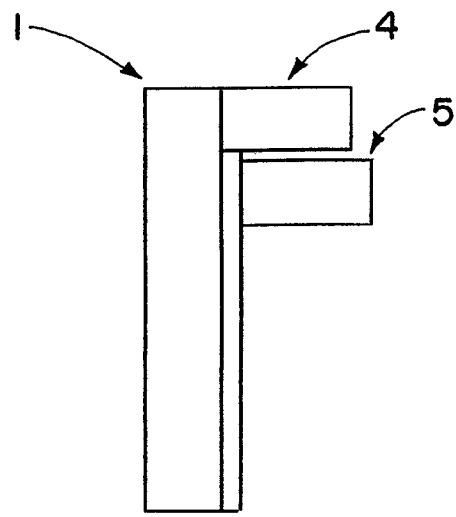

On the basis of FIG. 3, it is possible to illustrate how the stylet 1 can be placed on the catheter. Firstly, however, reference is to be made to FIGS. 4 and 5 which show how such a stylet 1' or 1 can be rolled from a film, wherein the longitudinal gap 2' or 2 can be formed or provided by keeping the longitudinal edges apart (FIG. 4) or by overlapping them (FIG. 5). FIGS. 6 and 7 show how a lever 4, 5, which in accordance with FIG. 5 is formed by overlapping longitudinal edges 2, can be provided at each of the upper ends of the stylet 1. When these levers 4, 5 are pressed together, the stylet 1 is elastically opened laterally, in order to form an access and to be placed over the line 10.

Returning now to FIG. 3, it then becomes clear that the fluid-guiding or drug-guiding line 10 which is supplied with the drug by the syringe 13 can be primed such that it is completely filled with the drug. The stylet 1 in accordance with the invention can then be placed on the part of the line 10 which protrudes upwards out of the catheter cover 20, by first pressing the levers 4, 5 together slightly in order to provide an access 2. When the film stylet then elastically bends together again, it will enclose the line 10. The stylet 1 can then be inserted down the line 10, into the catheter cover 20; if necessary for this purpose, it is opened slightly more with the aid of the levers 4, 5, in order to enable it to slide on the line 10. Ultimately, it will be positioned between the line 10 and the catheter cover 20, in the position shown in FIG. 1, and the catheter can be placed.

After placement, the stylet 1 can be moved back to the position in FIG. 3 and removed laterally and/or transversely (direction of the arrow) from the line 10, without the line 10 or its connection to the syringe (or pump) 13 having to be interrupted.

Figure 8:
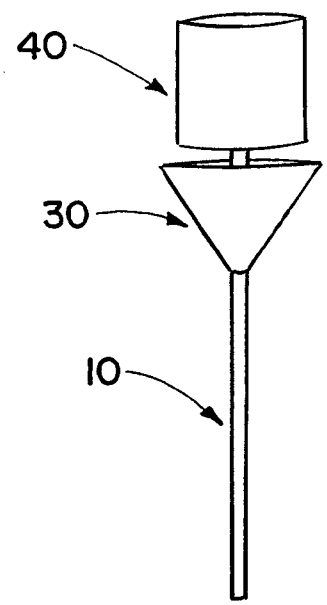
FIG. 8 shows a removing and/or opening device for a catheter in accordance with the invention.

In order to facilitate opening and/or removing such stylets, or also stylets formed from rolled material strips, a cone element or funnel element can be provided on the fluid-guiding line 10 in accordance with FIG. 8, in front of the adaptor 40 (for example, a Luer adaptor for connecting to the syringe), wherein said element has been identified in FIG. 8 by the reference sign 30. This cone element can open a stylet comprising a longitudinal gap, which is formed in the manner of a film and in the shape of a tube, when the stylet is pressed against the tip of the cone, so as to simplify removing the stylet from the line 10.

FIG. 9 is identical to FIG. 3 but includes a broken line 30 diagrammatically illustrating the weak point. The stylet can comprise a plurality of material layers or film layers, schematically illustrated by broken line in FIG. 6. The stylet can also comprise a different number of layers along the length of the stylet, schematically illustrated by broken line in FIG. 4.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments.

Although the invention has been shown and described with respect to one or more particular preferred embodiments, it is clear that equivalent amendments or modifications will occur to the person skilled in the art when reading and interpreting the text and enclosed drawings of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment or embodiments illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A catheter stylet for stiffening a catheter during a placing process, wherein the stylet comprises a tubular body having a proximal end, a distal end, a lumen for accommodating at least one fluid-guiding line of the catheter and an access for the lumen along which the stylet is configured to be elastically opened laterally to allow for removal of the stylet from around the fluid-guiding line in a direction substantially transverse to a longitudinal axis of the fluid-guiding line, and at least one lever that can be gripped to facilitate opening of the access, the lever having a proximal end and a distal end, the proximal end of the lever being proximate the proximal end of the body, wherein the body has an axial length extending from the distal end of the body to the distal end of the at least one lever that is greater than an axial length of the at least one lever, and wherein the stylet is formed from a film body configured to be altered in its diameter.

2. The catheter stylet according to claim 1, wherein the stylet comprises a substantially cylindrical or tubular, elongated body, and the lumen is the interior space of the body.

3. The catheter stylet according to claim 1, wherein the access comprises a longitudinal slit in the body of the stylet.

4. The catheter stylet according to claim 1, wherein the access comprises a weak point running longitudinally and/or axially on the stylet body.

5. The catheter stylet according to claim 4, wherein the weak point is a perforation of the stylet material.

6. The catheter stylet according to claim 1, wherein the access comprises two overlapping longitudinal edges on the body of the stylet.

7. The catheter stylet according to claim 1, wherein the stylet is gripped or altered in its diameter for opening or closing the access which is formed by two overlapping or mutually abutting stylet body longitudinal edges.

8. The catheter stylet according to claim 1, wherein the stylet comprises a plurality of material layers or film layers.

9. The catheter stylet according to claim 8, wherein the stylet comprises a different number of layers along the length of the stylet.

10. The catheter stylet according to claim 1, wherein the stylet is formed by at least one material strip which is rolled together at an angle.

11. The catheter stylet according to claim 10, wherein the at least one material strip is a film strip.

12. The catheter stylet according to claim 1, wherein the stylet comprises one or more of the following materials or is made from a material which exhibits one or more of the following material properties:
   a metal or metal film;
   a plastic or plastic film;
   a composite material or composite material film;
   a memory metal or memory alloy;
   a material which is CT-compatible and/or visible in CT images;
   a material which is MR-compatible and/or visible in MR images;
   a biocompatible material.

13. The catheter stylet according to claim 12, wherein the plastic or plastic film is a polymer.

14. The catheter stylet according to claim 13, wherein the polymer is PE, PP or PEEK.

15. A catheter stylet catheter system, comprising: a stylet in accordance with claim 1; and a catheter which comprises a fluid-guiding line.

16. The system according to claim 15, wherein the catheter comprises an interior fluid-guiding line and an exterior covering catheter part, and the stylet is provided for insertion between the line and the covering catheter part, such that it surrounds the line and is surrounded by the covering catheter part.

17. A method for stiffening a catheter during the placing process, wherein a stylet which comprises a lumen arranged around at least one fluid-guiding line of the catheter, wherein a stylet in accordance with claim 1 is used.

18. A catheter stylet for stiffening a catheter during a placing process, wherein the stylet comprises a tubular plastic or metal body having a proximal end, a distal end, a lumen for accommodating at least one fluid-guiding line of the catheter and an access for the lumen along which the stylet is configured to be elastically opened laterally to allow for removal of the stylet from around the fluid-guiding line in a direction substantially transverse to a longitudinal axis of the fluid-guiding line, and a pair of levers that can be gripped to facilitate opening of the access, wherein the levers are attached to the body at respective opposite sides of the access and are axially staggered with respect to one another.

19. A catheter stylet for stiffening a catheter during a placing process, wherein the stylet comprises a tubular body having a proximal end, a distal end, a lumen for accommodating at least one fluid-guiding line of the catheter and an access for the lumen along which the stylet is configured to be elastically opened laterally to allow for removal of the stylet from around the fluid-guiding line in a direction substantially transverse to a longitudinal axis of the fluid-guiding line, wherein the stylet is configured to completely circumferentially surround the fluid-guiding line in an unflexed condition and wherein the access comprises two overlapping longitudinal edges on the body of the stylet.

20. A catheter stylet for stiffening a catheter during a placing process, wherein the stylet comprises a tubular body having a proximal end, a distal end, a lumen for accommodating at least one fluid-guiding line of the catheter and an access for the lumen along which the stylet is configured to be elastically opened laterally to allow for removal of the stylet from around the fluid-guiding line in a direction substantially transverse to a longitudinal axis of the fluid-guiding line, and at least one lever that can be gripped to facilitate opening of the access, the lever having a proximal end and a distal end, the proximal end of the lever being proximate the proximal end of the body, wherein the body has an axial length extending from the distal end of the body to the distal end of the at least one lever that is greater than an axial length of the at least one lever, and wherein the stylet is a rolled film stylet.

* * * * *